United States Patent
Hwang et al.

(10) Patent No.: US 6,416,475 B1
(45) Date of Patent: *Jul. 9, 2002

(54) ULTRASONIC SIGNAL PROCESSOR FOR A HAND HELD ULTRASONIC DIAGNOSTIC INSTRUMENT

(75) Inventors: Juin-Jet Hwang, Mercer Island; Geoffrey H. Jones, Seattle; Terrence R. Doherty, Snohomish; Lauren S. Pflugrath, Seattle, all of WA (US)

(73) Assignee: Sonosite, Inc., Bothell, WA (US)

( * ) Notice: Subject to any disclaimer, the term of this patent is extended or adjusted under 35 U.S.C. 154(b) by 73 days.

This patent is subject to a terminal disclaimer.

(21) Appl. No.: 09/630,165

(22) Filed: Aug. 1, 2000

Related U.S. Application Data

(63) Continuation-in-part of application No. 09/167,964, filed on Oct. 6, 1998, now Pat. No. 6,135,961, and a continuation-in-part of application No. 08/863,937, filed on May 27, 1997, now Pat. No. 5,817,024, and a continuation-in-part of application No. 08/826,543, filed on Apr. 3, 1997, now Pat. No. 5,893,363, and a continuation-in-part of application No. 08/672,782, filed on Jun. 28, 1996, now Pat. No. 5,722,412.

(51) Int. Cl.$^7$ ............................. A61B 8/00; A61B 8/06
(52) U.S. Cl. ...................................... 600/441; 600/455
(58) Field of Search .................... 600/437, 440–441, 600/443, 447, 454–456, 367, 138.7

(56) References Cited

U.S. PATENT DOCUMENTS

| | | | |
|---|---|---|---|
| 5,590,658 A | 1/1997 | Chiang et al. | 128/661.01 |
| 5,709,209 A | 1/1998 | Friemel et al. | 128/660.07 |
| 5,722,412 A | 3/1998 | Pflugrath et al. | 128/662.03 |
| 5,817,024 A | 10/1998 | Ogle et al. | 600/447 |
| 5,893,363 A | 4/1999 | Little et al. | 600/447 |
| 6,135,961 A | 10/2000 | Pflugrath et al. | 600/447 |

*Primary Examiner*—Francis J. Jaworski
(74) *Attorney, Agent, or Firm*—Townsend and Townsend and Crew LLP

(57) ABSTRACT

A hand held ultrasonic instrument is provided in a portable unit which performs both B mode and Doppler imaging. The instrument includes a transducer array mounted in a hand-held enclosure, with an integrated circuit transceiver connected to the elements of the array for the reception of echo signals. A digital signal processing circuit performs both B mode and Doppler signal processing such as filtering, detection and Doppler estimation, as well as advanced functions such as assembly of multiple zone focused scanlines, synthetic aperture formation, depth dependent filtering, speckle reduction, flash suppression, and frame averaging.

12 Claims, 7 Drawing Sheets

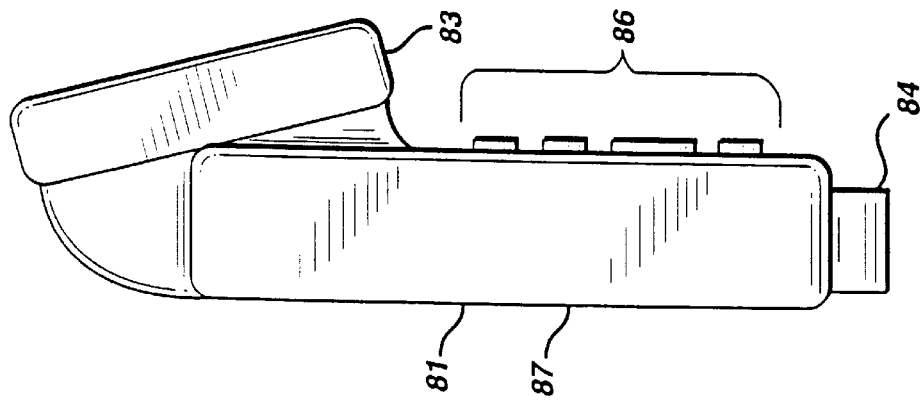
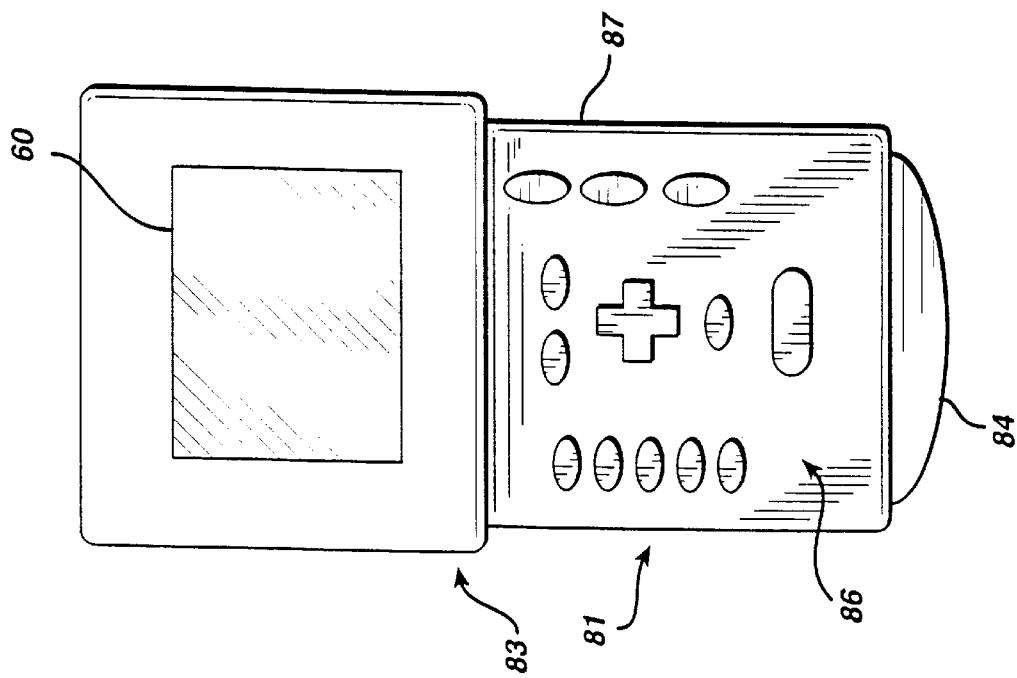

FIG. 8

| SWITCH FUNCTION | DESCRIPTION | NUMBER OF CONTACTS |
|---|---|---|
| POWER OFF/ON | SLIDE SWITCH | 1 |
| ACTIVE SCAN/FREEZE | PUSH AND HOLD FOR ACTIVE SCAN | 1 |
| CPA | ENABLES AND DISABLES COLOR POWER ANGIO CPA | 1 |
| DOPPLER/CPA FILTER | HIGH/MEDIUM/LOW BUTTON CYCLES THROUGH 3 SELECTIONS | 1 |
| 3D IMAGING MODE | ENABLES 3D CAPTURE WHEN ENGAGED BEFORE THE ACTIVE SCAN BUTTON IS PUSHED | 1 |
| PRINT | SENDS SERIAL SIGNAL TO PRINTER | 1 |
| CURSOR POSITION | X/Y POSITION OF CURSOR | 4 |
| ENTER | ENTERS SELECTION | 1 |
| MENU | TOGGLES MENU FUNCTIONS OFF AND ON, USES CURSOR AND ENTER. FUNCTIONS: APPLICATION SELECTION USED TO ENTER ALPHA NUMERIC DATA, PATIENT ID, PATIENT NAME, CINE 2D AND 3D REVIEW | 1 |
| MEASURE | ENABLES MEASUREMENTS, USES CURSOR AND ENTER | 1 |
| FOCUS | ENABLES FOCUS MODE, CURSOR UP DOWN POSITIONS FOCUS, CURSOR LEFT RIGHT SELECTS NUMBER OF ZONES | 1 |
| IMAGE | ALLOWS THE USER TO SELECT THROUGH SEVERAL GRAY SCALE CURVES, SPATIAL AND TEMPORAL FILTERS WITH IN A PREDETERMINED SET OF SETUPS FOR A SELECTED APPLICATION | 2 |
| DEPTH | UP/DOWN, 5 DEPTH SELECTIONS | 2 |
| TGC GAIN | UP/DOWN | 2 |
| BRIGHTNESS | LCD DISPLAY CONTROL UP/DOWN | 2 |
| CONTRAST | LCD DISPLAY CONTROL UP/DOWN | 2 |

ULTRASONIC SIGNAL PROCESSOR FOR A HAND HELD ULTRASONIC DIAGNOSTIC INSTRUMENT

This application is a continuation and claims the benefit of priority from U.S. Continuation in Part (CIP) application Ser. No. 09/167,964, filed Oct. 6, 1998 now U.S. Pat. No. 6,135,961; application Ser. No. 08/672,782 filed Jun. 28, 1996, now U.S. Pat. No. 5,722,412; application Ser. No. 08/826,543 filed Apr. 3, 1997, now U.S. Pat. No. 5,893,363; and application Ser. No. 08/863,937 filed May 27, 1997, now U.S. Pat. No. 5,817,024, the disclosure of which is incorporated by reference.

This invention relates to medical ultrasonic diagnostic systems and, in particular, to a fully integrated hand held ultrasonic diagnostic instrument.

As is well known, modern ultrasonic diagnostic systems are large, complex instruments. Today's premium ultrasound systems, while mounted in carts for portability, continue to weigh several hundred pounds. In the past, ultrasound systems such as the ADR 4000 ultrasound system produced by Advanced Technology Laboratories, Inc., assignee of the present invention, were smaller, desktop units about the size of a personal computer. However, such instruments lacked many of the advanced features of today's premium ultrasound systems such as color Doppler imaging and three dimensional display capabilities. As ultrasound systems have become more sophisticated they have also become bulkier.

However, with the ever increasing density of digital electronics, it is now possible to foresee a time when ultrasound systems will be able to be miniaturized to a size even smaller than their much earlier ancestors. The physician is accustomed to working with a hand held ultrasonic scanhead which is about the size of an electric razor. It would be desirable, consistent with the familiar scanhead, to be able to compact the entire ultrasound system into a scanhead-sized unit. It would be further desirable for such an ultrasound instrument to retain as many of the features of today's sophisticated ultrasound systems as possible, such as speckle reduction, color Doppler and three dimensional imaging capabilities.

In accordance with the principles of the present invention, a diagnostic ultrasound instrument is provided which exhibits many of the features of a premium ultrasound system in a hand held unit. These premium system features are afforded by a digital signal processor capable of performing both greyscale and Doppler signal processing including their associated filtering, compression, flash suppression and mapping functions, as well as advanced features such as synthetic aperture formation, multiple focal zone imaging, frame averaging, depth dependent filtering, and speckle reduction. In a preferred embodiments the digital signal processor is formed on a single integrated circuit chip. This sophisticated ultrasound instrument can be manufactured as a hand held unit weighing less than five pounds.

In the drawings:

FIGS. 2a and 2b are front and side views of a hand-held ultrasound system of the present invention which is packaged as a single unit;

FIG. 8 is a chart of the user controls of the ultrasound system of FIG. 1.

Figure 1:
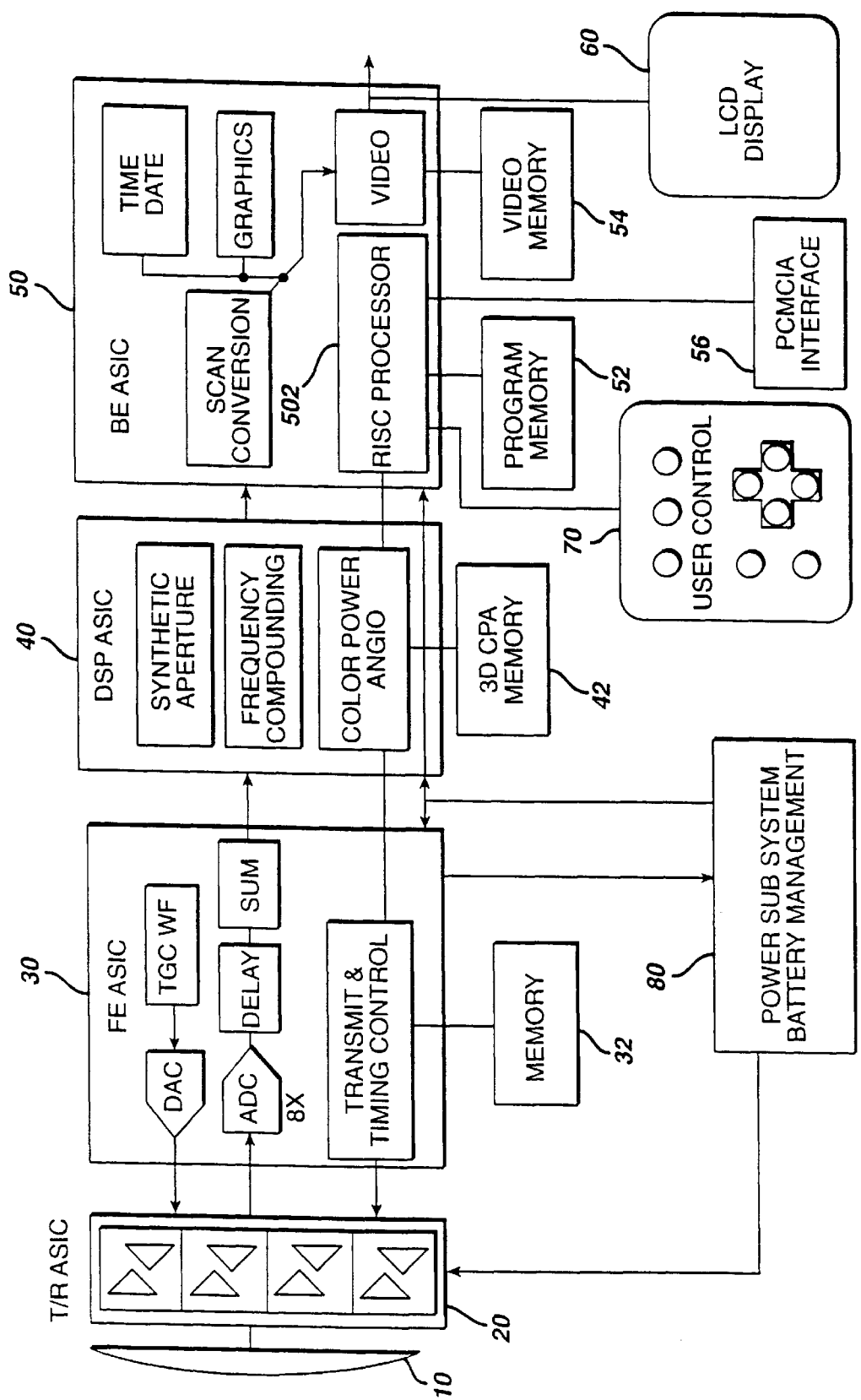
FIG. 1 illustrates in block diagram form the architecture of a hand-held ultrasound system of the present invention.

Referring first to FIG. 1, the architecture of a hand-held ultrasound system of the present invention is shown. It is possible to package an entire ultrasound system in a single hand-held unit only through judicious selection of functions and features and efficient use of integrated circuit and ultrasound technology. A transducer array 10 is used for its solid state, electronic control capabilities, variable aperture, image performance and reliability. Either a flat or curved linear array can be used. In a preferred embodiment the array is a curved array, which affords a broad sector scanning field. While the preferred embodiment provides sufficient delay capability to both steer and focus a flat array such as a phased array, the geometric curvature of the curved array reduces the steering delay requirements on the beamformer. The elements of the array are connected to a transmit/receive ASIC 20 which drives the transducer elements and receives echoes received by the elements. The transmit/receive ASIC 20 also controls the active transmit and receive apertures of the array 10 and the gain of the received echo signals. The transmit/receive ASIC is preferably located within inches of the transducer elements, preferably in the same enclosure, and just behind the transducer. A preferred embodiment of the transmit/receive ASIC is described in detail in U.S. patent application Ser. No. [ATL-152] filed Apr. 3, 1997 and entitled ULTRASONIC ARRAY TRANSDUCER TRANSCEIVER FOR A HAND HELD ULTRASONIC DIAGNOSTIC INSTRUMENT.

Echoes received by the transmit/receive ASIC 20 are provided to the adjacent front end ASIC 30, which beamforms the echoes from the individual transducer elements into coherent scanline signals. The front end ASIC 30 also controls the transmit waveform timing, aperture and focusing of the ultrasound beam through control signals provided for the transmit/receive ASIC. In the illustrated embodiment the front end ASIC 30 provides timing signals for the other ASICs and time gain control. A power and battery management subsystem 80 monitors and controls the power applied to the transducer array, thereby controlling the acoustic energy which is applied to the patient and minimizing power consumption of the unit. A memory device 32 is connected to the front end ASIC 30, which stores data used by the beamformer. A preferred embodiment of the front end ASIC is described in detail in U.S. Pat. 5,817,024 for HAND HELD ULTRASONIC DIAGNOSTIC INSTRUMENT WITH DIGITAL BEAMFORMER.

Beamformed scanline signals are coupled from the front end ASIC 30 to the digital signal processing ASIC 40. The digital signal processing ASIC 40 filters the scanline signals, processes them as B mode signals, Doppler signals, or both, and in the preferred embodiment also provides several advanced features including synthetic aperture formation, frequency compounding, Doppler processing such as power Doppler (color power angio) processing, and speckle reduction as more fully detailed below.

The ultrasound B mode and Doppler information is then coupled to the adjacent back end ASIC 50 for scan conversion and the production of video output signals. A memory device 42 is coupled to the back end ASIC 50 to provide storage used in three dimensional power Doppler (3D CPA)

imaging. The back end ASIC also adds alphanumeric information to the display such as the time, date, and patient identification. A graphics processor overlays the ultrasound image with information such as depth and focus markers and cursors. Frames of ultrasonic images are stored in a video memory 54 coupled to the back end ASIC 50, enabling them to be recalled and replayed in a live Cineloop® realtime sequence. Video information is available at a video output in several formats, including NTSC and PAL television formats and RGB drive signals for an LCD display 60 or a video monitor.

The back end ASIC 50 also includes the central processor for the ultrasound system, a RISC (reduced instruction set controller) processor 502. The RISC processor is coupled to the front end and digital signal processing ASICs to control and synchronize the processing and control functions throughout the hand-held unit. A program memory 52 is coupled to the back end ASIC 50 to store program data which is used by the RISC processor to operate and control the unit. The back end ASIC 50 is also coupled to a data port configured as an infrared transmitter or a PCMCIA interface 56. This interface allows other modules and functions to be attached to or communicate with the hand-held ultrasound unit. The interface 56 can connect to a modem or communications link to transmit and receive ultrasound information from remote locations. The interface can accept other data storage devices to add new functionality to the unit, such as an ultrasound information analysis package.

The RISC processor is also coupled to the user controls 70 of the unit to accept user inputs to direct and control the operations of the hand-held ultrasound system.

Power for the hand-held ultrasound system in a preferred embodiment is provided by a rechargeable battery. Battery power is conserved and applied to the components of the unit from the power subsystem 80. The power subsystem 80 includes a DC converter to convert the low battery voltage to a higher voltage which is applied to the transmit/receive ASIC 20 to drive the elements of the transducer array 10.

FIGS. 2a and 2b illustrate a one piece unit 87 for housing the ultrasound system of FIG. 1. The front of the unit is shown in FIG. 2a, including an upper section 83 which includes the LCD display 60. The lower section 81 includes the user controls as indicated at 86. The user controls enable the user to turn the unit on and off, select operating characteristics such as the mode (B mode or Doppler), color Doppler sector or frame rate, and special functions such as three dimensional display. The user controls also enable entry of time, date, and patient data. A four way control, shown as a cross, operates as a joystick to maneuver cursors on the screen or select functions from a user menu. Alternatively a mouse ball or track pad can be used to provide cursor and other controls in multiple directions. Several buttons and switches of the controls are dedicated for specific functions such as freezing an image and storing and replaying an image sequence from the Cineloop memory.

At the bottom of the unit 87 is the aperture 84 of the curved transducer array 10. In use, the transducer aperture is held against the patient to scan the patient and the ultrasound image is displayed on the LCD display 60.

FIG. 2b is a side view of the unit 87, showing the depth of the unit. The unit is approximately 20.3 cm high, 11.4 cm wide, and 4.5 cm deep. This unit contains all of the elements of a fully operational ultrasound system with a curved array transducer probe, in a single package weighing less than five pounds. A major portion of this weight is attributable to the battery housed inside the unit.

Figure 4:
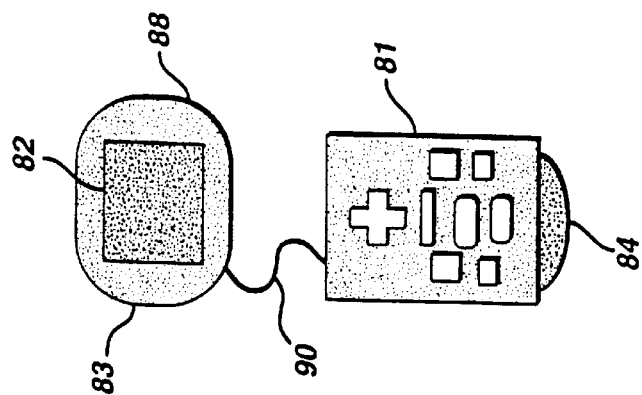
FIG. 4 illustrates the two units of a hand-held ultrasound system of the present invention in a two-unit package.
Figure 3B:
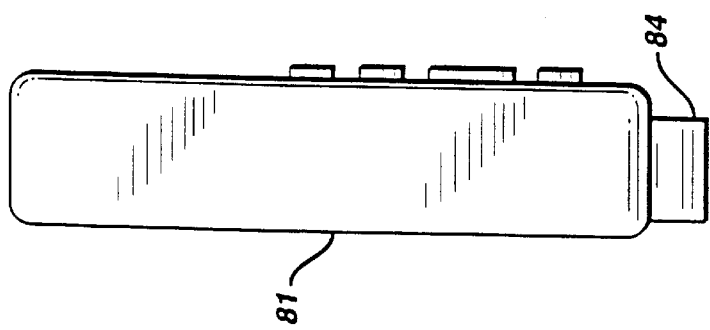
FIGS. 3a and 3b are front and side views of the transducer unit of a two-unit hand-held ultrasound system of the present invention.
Figure 3A:
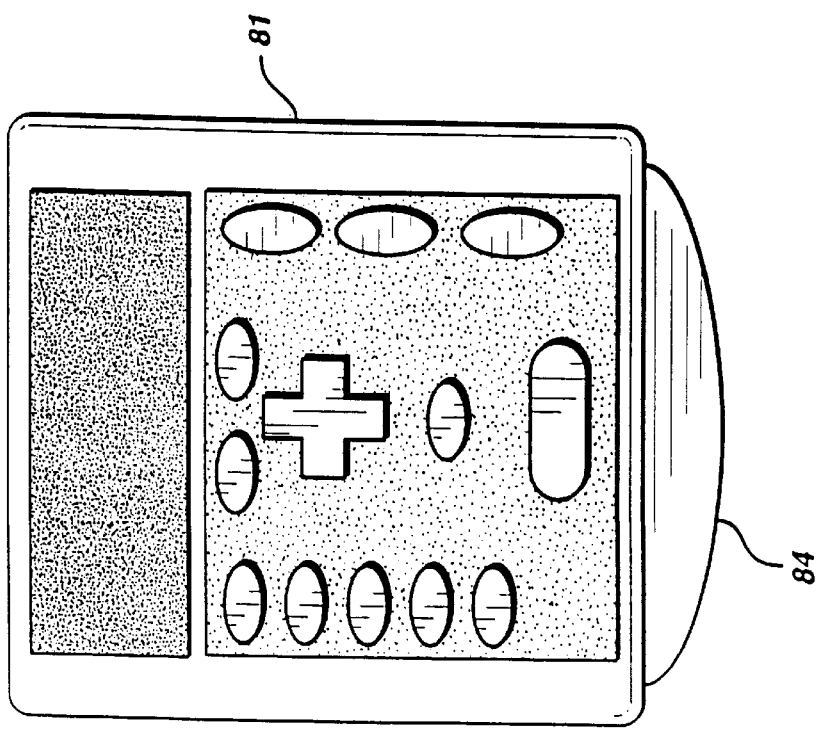

FIGS. 3 and 4 illustrate a second packaging configuration in which the ultrasound system is housed in two separate sections. A lower section 81 includes the transducer array, the electronics through to a video signal output, and the user controls. This lower section is shown in FIG. 3a, with the curved transducer array aperture visible at the bottom. The lower section is shown in the side view of FIG. 3b. This lower section measures about 11.4 cm high by 9.8 cm wide by 2.5 cm deep. This unit has approximately the same weight as a conventional ultrasound scanhead. This lower section is connected to an upper section 83 as shown in FIG. 4 by a cable 90. The upper section 83 includes an LCD display 82 and a battery pack 88. The cable 90 couples video signals from the lower unit 81 to the upper unit for display, and provides power for the lower unit from the battery pack 88. This two part unit is advantageous because the user can maneuver the lower unit and the transducer 84 over the patient in the manner of a conventional scanhead, while holding the upper unit in a convenient stationary position for viewing. By locating the battery pack in the upper unit, the lower unit is lightened and easily maneuverable over the body of the patient.

Other system packaging configurations will be readily apparent. For instance, the front end ASIC 30, the digital signal processing ASIC 40, and the back end ASIC 50 could be located in a common enclosure, with the beamformer of the front end ASIC connectable to different array transducers. This would enable different transducers to be used with the digital beamformer, digital filter, and image processor for different diagnostic imaging procedures. A display could be located in the same enclosure as the three ASICS, or the output of the back end ASIC could be connected to a separate display device. Alternatively, the transducer array 10, transmit/receive ASIC 20 and front end ASIC 30 could be in the transducer enclosure and the balance of the system in the battery and display unit. The configuration of FIG. 4 could be changed to relocate the user controls onto the display and battery pack unit, with the ultrasound ASICs located in the unit with the transducer array.

Figure 5:
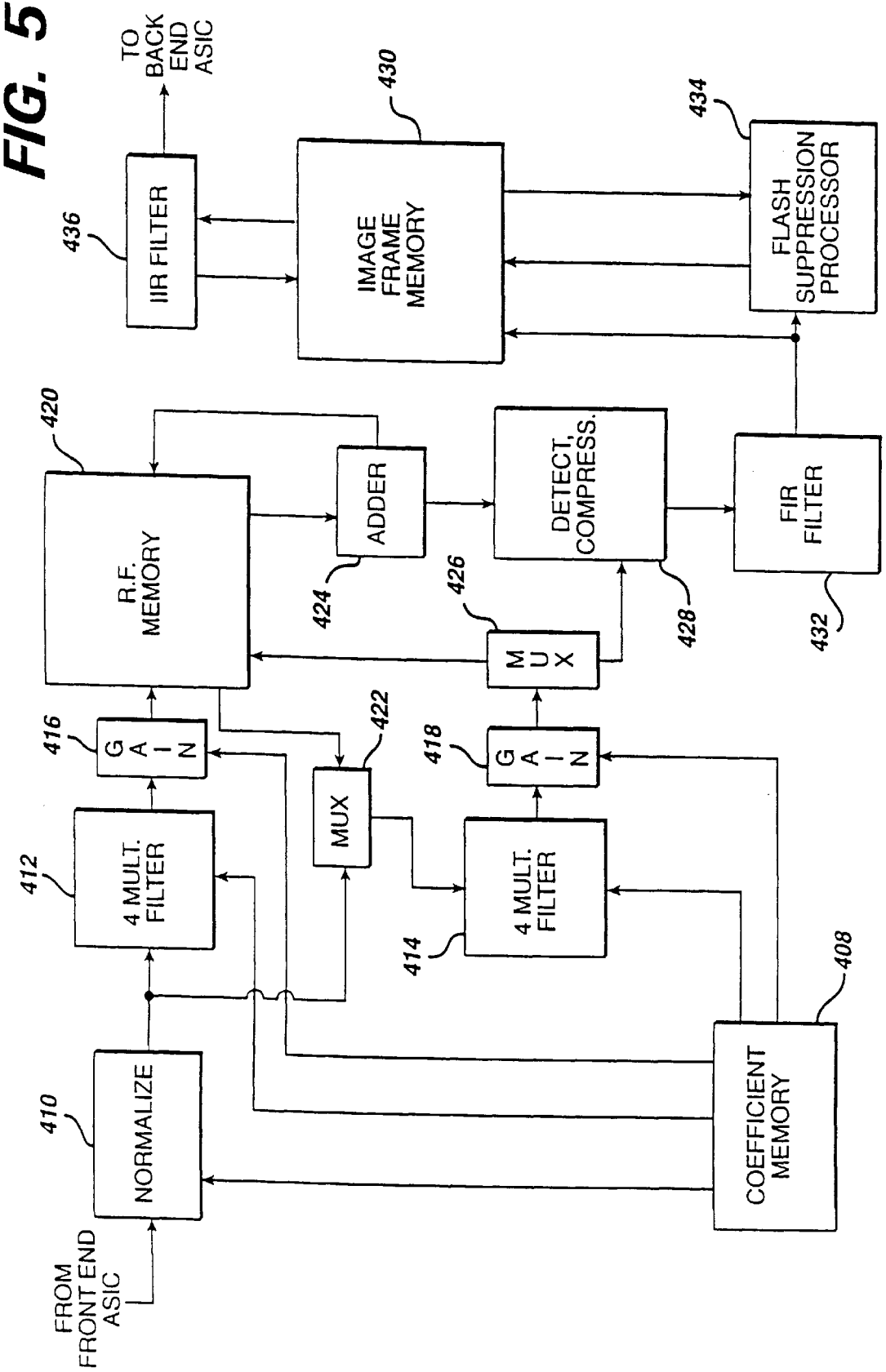
FIG. 5 is a block diagram of the digital signal processing ASIC of the ultrasound system of FIG. 1.

Referring to FIG. 5, a detailed block diagram of the digital signal processing ASIC 40 is shown. Scanline signals from the front end ASIC 30 are received by a normalization circuit 410, where they are multiplied by a variable coefficient supplied by coefficient memory 408 to normalize the received signals for aperture variation. When the transducer is receiving signals along the scanline from shallow depths, a relatively small aperture, such as four or eight transducer elements, is used to receive echo signals. As the reception depth along the scanline increases, the aperture is incrementally increased so that the full 32 element aperture is used at maximum depths. The normalization circuit 410 will multiply the received scanline signals by appropriate coefficients over the range of aperture variation, such as factors of four or eight, to normalize the signals for this aperture variation effect.

Figure 6:
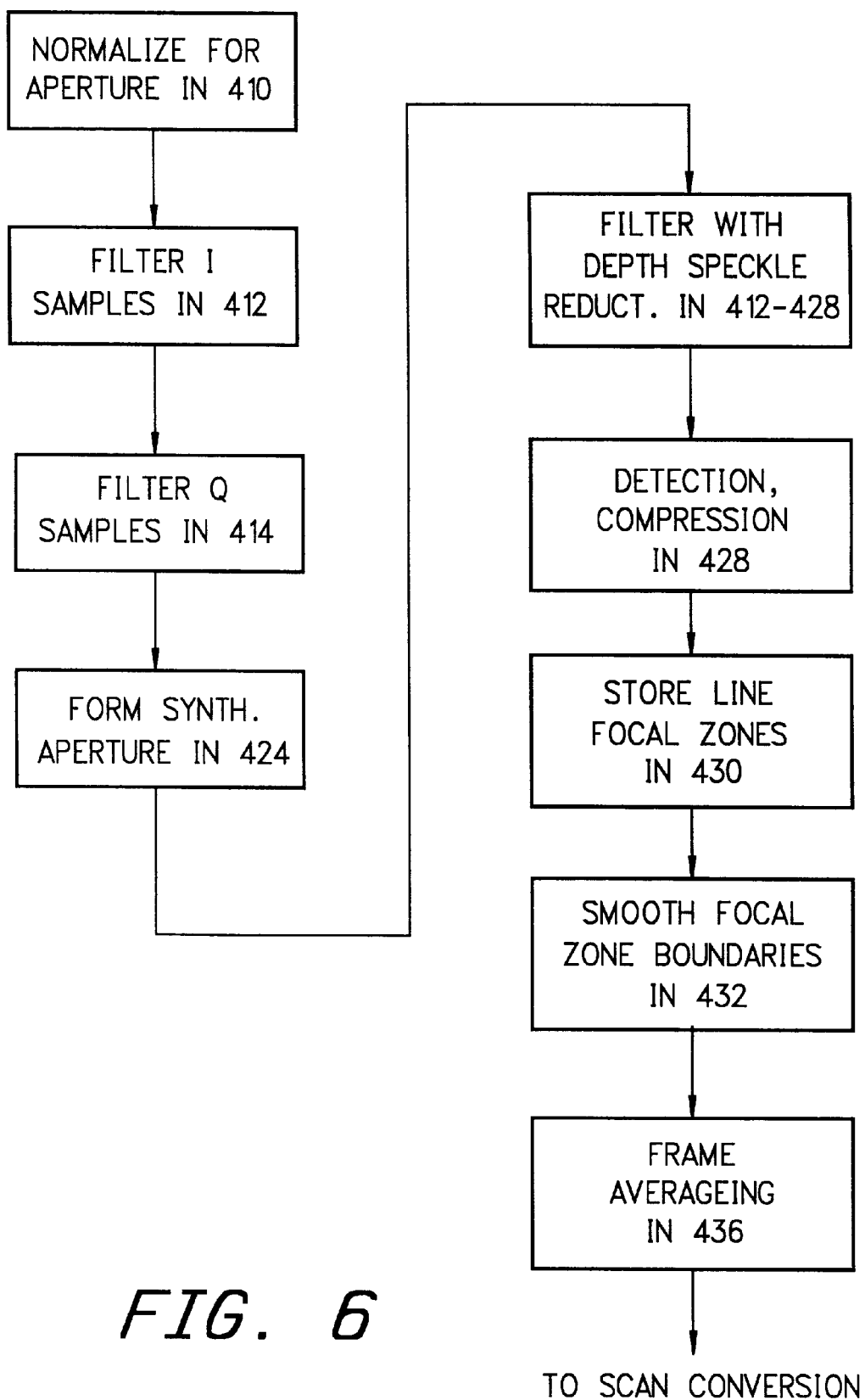
FIG. 6 is a flowchart of B mode processing by the digital signal processing ASIC.

When the ultrasound system is operated in the B mode to form a structural image of tissue and organs, the digital signal processor is operated as shown by the flowchart of FIG. 6. The normalized echo signals follow two paths in FIG. 5, one of which is coupled to a four multiplier filter 412 and the other of which is coupled by a multiplexer 422 to a second four multiplier filter 414. Each multiplier filter includes a multiplier and an accumulator which operate as an FIR (finite impulse response) filter. Scanline echo signals are shifted sequentially into a multiplier, multiplied by coefficients supplied by the coefficient memory 408, and the products are accumulated in the accumulator at the output of the multiplier. The coefficients for the filter 412 are chosen to multiply the echo signals by a cosine function and the coefficients for the filter 414 are chosen to multiply the echo signals by a sine function, preparatory for I and Q quadrature signal detection. The four multiplier filters produce accumulated signals at a rate which is less than the input rate to the multipliers, thereby performing decimation band pass filtering. When the signal bandwidth exceeds the display bandwidth of the display monitor, the image lines will flicker due to an aliasing condition. The decimation filtering is designed to reduce the signal bandwidth as well as the data rate to match the display bandwidth of the monitor. By applying a succession of input signals and coefficients to a multiplier and accumulating intermediate products, the effective length of the filter can be increased. For instance, input signals 1–8 can be sequentially weighted by the fourth multiplier and the products accumulated in the fourth accumulator; input signals 3–10 can be weighted by the third multiplier and the products accumulated in the third accumulator; input signals 5–12 can be weighted by the second multiplier and the products accumulated in the second accumulator; and input signals 7–14 can be weighted by the first multiplier and the products accumulated in the first accumulator. The data rate has thereby been decimated by two, and each multiplier and accumulator is effectively operated as an eight tap filter. Thus it is seen that the effective number of taps of the filter is a product of the number of multipliers (four in this example) and the decimation rate (two in this example).

Additionally, this filter reduces r.f. noise and quantization noise through its bandwidth limiting effects. I and Q echo signal samples are produced at the outputs of filters 412 and 414, amplified if desired by the multipliers of gain stages 416 and 418, then stored in the r.f. memory 420. The Q samples are coupled to the r.f. memory by a multiplexer 426.

When a synthetic aperture image is to be formed, partially summed scanlines from a portion of the full aperture are acquired following separate pulse transmissions, then combined to form full aperture scanlines. When the synthetic aperture is formed from two pulse transmissions, the I and Q samples from the scanline of the first half of the aperture are stored in the r.f. memory 420 until the I and Q samples from the other half of the aperture are received. As the samples from the second half of the aperture are received, they are combined with their spatially corresponding counterparts by an adder 424. The size of the r.f. memory is kept to a minimum by storing the aperture signals after decimation filtering, which reduces the size of the memory required to store the scanline signal samples.

After the I and Q samples for the full aperture have been formed, the echo samples are coupled from the adder 424 to a detection and compression circuit 428. This circuit includes two shift registers and a multiplier arranged to form a CORDIC processor for performing envelope detection of the form $(I^2+Q^2)^{1/2}$. See, for instance, "The CORDIC Trigonometric computing Technique, by J. E. Volder, *IRE Trans. on Elect. Computers*, (September 1959). The detected signal is compressed and scaled to map the detected signals to a desired range of display gray levels.

Following detection and compression mapping, the grayscale signals are lowpass filtered in an FIR filter 432, then stored in an image. frame memory 430. If the selected scanning made utilizes a single transmit focal point, the grayscale signals are transmitted to the back end ASIC 50 for scan conversion. Prior to leaving the ASIC 40, the greyscale signals can be frame averaged by an infinite impulse response (IIR) filter 436 which utilizes image frame memory 430 as a frame buffer and incorporates one multiplier and two adders to perform frame to frame averaging of the form $$F_{out}=(1-\alpha)\ F_{out-1}+\alpha F_{new}=F_{out-1}+\alpha(F_{new}-F_{out-1})$$

where the multiplier coefficient is $\alpha$. If the coefficient is a binary number (e.g.,0.5, 0.25, 0.125) Fout can be obtained with an add-shift-add operation.

If multiple focal zones are used, each received scanline segment is stored in the r.f. memory 420 until scanline segments from the entire display depth have been received. Preferably the scanline segments for one complete focal zone are acquired before transmitting and receiving segments from another focal zone. When all segments for a scanline have been acquired, each complete scanline is then read out of the r.f. memory and filtered by the FIR filter 432, which smoothes the boundaries between the segments for a more pleasing, artifact-free image.

If both multiple zone focusing and synthetic aperture are used, the scanline segments of both halves of the aperture are received over the full focal zone and assembled in the r.f memory 420. Corresponding scanline segments are then received from other focal zones and joined with the segments from the first received focal zone. The completed scanlines are then filtered by FIR filter 432 to smooth the boundaries between segments.

The user may choose to process the grayscale image with certain image enhancement features, such as depth dependent filtering or speckle reduction such as the frequency compounding technique described in U.S. Pat. No. 4,561,019. These optional processing techniques necessitate the use of the filters 412 and 414 for separate bandpass filtering of the scanline signals and absolute value detection rather than quadrature detection. In the case of depth dependent filtering the received echo signals are multiplied by cosine functions in both of filters 412 and 414, but with coefficients chosen so that one filter produces output signals in a high passband and the other produces output signals in a low passband. The output signals produced by the two filters are of the form $I_1=h_1(t)\cos \omega_H t$ and $I_2=h_2(t)\cos \omega_L t$. These two output signals are amplified in gain stages 416 and 418 by complementary time varying gain control functions. The high frequency passband signals $I_1$ are initially amplified strongly, then the gain is decreased as echo signals are received from increasing depths along the scanline. In a complementary manner the low frequency passband signals $I_2$ are initially at a low level, then amplified in an increasing manner with depth as the high frequency gain is rolled off. Thus, signals at shallow depths will exhibit a relatively high passband, and signals from greater depths will pass through a relatively lower passband which reduces high frequency noise at the greater depths. Detection in the CORDIC processor of circuit 428 is performed by absolute value detection by squaring $I_1$ and $I_2$, then summing the results. Following summation the signals are log compressed to the desired grayscale mapping characteristic. Alternatively, the signals passed by the separate passbands are summed by the adder 424, then detected by absolute value detection in the detection and compression circuitry 428 and mapped.

The same processors can be used to provide speckle reduction by frequency compounding. The coefficients of one of the filters 412,414 are chosen to filter the received signals by a high frequency passband, and the coefficients of the other filter are chosen to filter the received signals by a contiguous low frequency passband. The coefficients of the gain stages 416,418 are chosen to equalize the responses of the two passbands. The signals of the high and low passbands are coupled to the detection and compression circuitry where the passbands are separately detected through absolute value detection as described above, then the detected signals are log compressed to the desired grayscale mapping characteristic and summed on a spatial basis.

Figure 7:
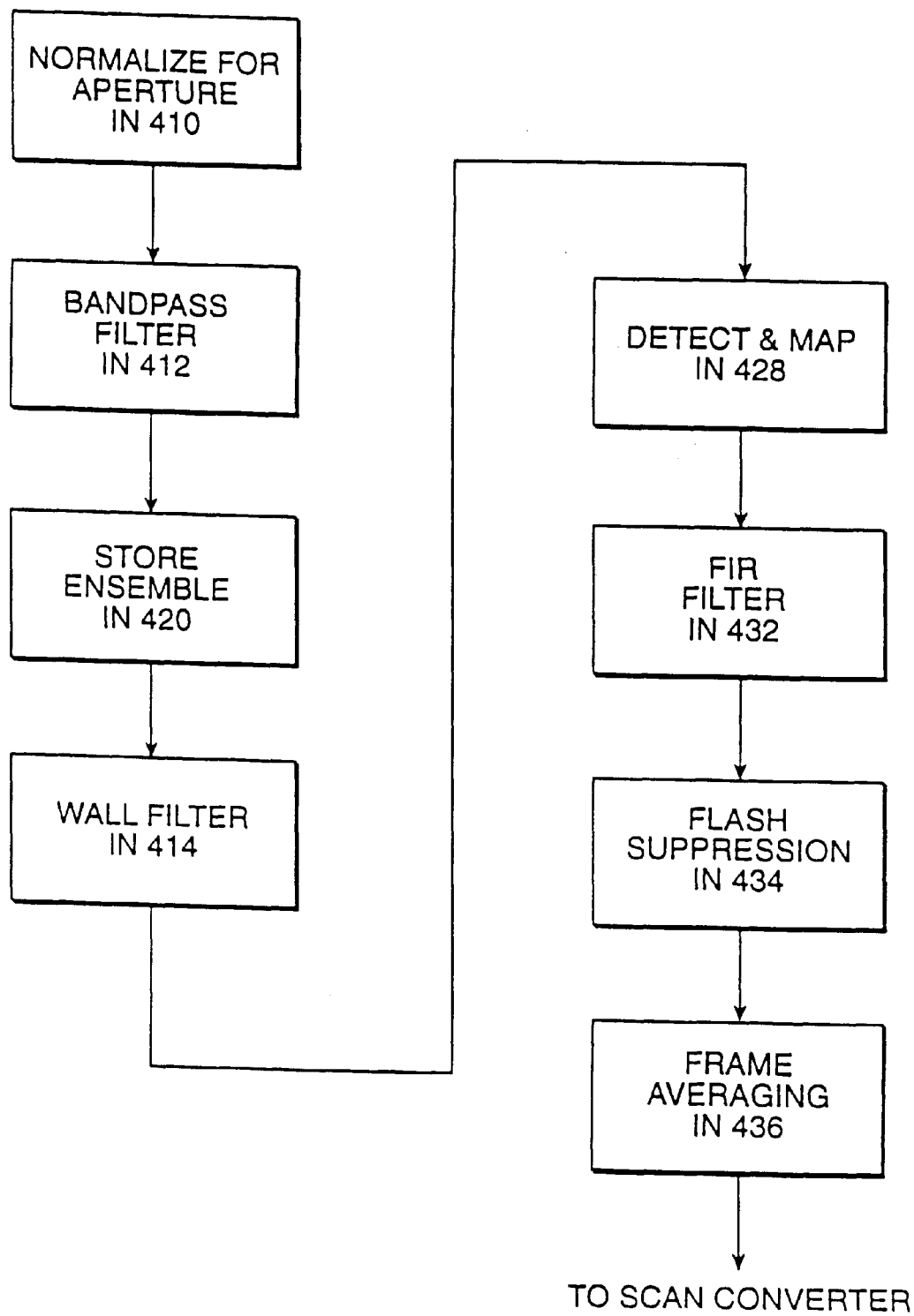
FIG. 7 is a flowchart of Doppler processing by the digital signal processing ASIC.

The processing of Doppler echo signals for power Doppler (CPA) display is shown in FIG. 5 together with the flowchart of FIG. 7. Each scanline vector is scanned repetitively, for instance eight times, to assemble an ensemble of Doppler information along the vector. Each received scanline of echo signals is normalized by the normalization circuit 410 and undergoes decimation band pass filtering in the filter 412. Each scanline of the ensemble is stored in the r.f. memory 420 until a complete ensemble has been accumulated. The scanlines of each ensemble are coupled by the multiplexer 422 to the four multiplier filter 414, which performs wall filtering and Doppler power estimation through matrix filtering. Wall filtering is performed by selection of appropriate multiplier coefficients and the matrix filtering is of the form $$\begin{bmatrix} y_1 \\ y_2 \\ y_3 \\ \vdots \\ y_n \end{bmatrix} = \begin{bmatrix} a_{11} & a_{12} & a_{13} & \cdots & a_{1n} \\ b_{11} & b_{12} & b_{13} & \cdots & b_{1n} \\ c_{11} & c_{12} & c_{13} & \cdots & c_{1n} \\ \vdots & \vdots & \vdots & & \vdots \\ z_{11} & z_{12} & z_{13} & \cdots & z_{1n} \end{bmatrix} \cdot \begin{bmatrix} x_1 \\ x_2 \\ x_3 \\ \vdots \\ x_n \end{bmatrix}$$

where $x_1 \ldots x_n$ are spatially aligned signals from the ensemble of scanlines and $Y_1 \ldots y_n$ are output Doppler values. In a preferred embodiment a four multiplier filter is used for matrix filtering, and the filtering is performed sequentially and incrementally. Intermediate products are accumulated as described above, thereby extending the filter length. For example, in processing the above matrix with a four multiplier filter, the intermediate products $a_{11}x_1+a_{12}x_2+a_{13}x_3+a_{14}x_4$ are formed initially and summed in the accumulator. Then products $a_{15}x_5+a_{16}x_6+a_{17}x_7+a_{18}x_8$ are formed by the multipliers and summed in the accumulator with the previously computed intermediate products. By accumulating intermediate products in this manner the four multipliers and accumulator can be extended to a filter of any desired length, restricted only by the maximum processing time available. The Doppler values are coupled to the detection and compression circuitry 428 through the gain stage 418 and the multiplexer 426, where the Doppler signal amplitude at each echo location along the scanline is detected through absolute value detection of the form $$y = \sum_{n}^{1-n} y_n^2$$

The Doppler values y are compressed and scaled using the CORDIC processor of the detection and compression circuitry 428.

Once the Doppler signal amplitude values have been detected and filtered by FIR filter 432, the resulting values are spatially stored and image clutter is removed by a flash suppression processor 434, which eliminates large frame to frame variations in the displayed signals. Flash suppression processor 434 may operate by any of a number of known flash suppression techniques, such as frame to frame comparison and elimination or the notch filtering technique of U.S. Pat. No. 5,197,477. A preferred technique for flash suppression processing is min-max filtering as described in detail in the parent U.S. patent application Ser. No. 08/672,782.

The image frame memory 430 is capable of storing either a gray scale frame or a power Doppler frame. Each frame can be temporally filtered by the IIR filter 436, which performs frame averaging on a point-by-point basis as described above. The temporally filtered image information is then provided to the back end ASIC 50 for scan conversion and display.

The sequences of operating the digital signal processing ASIC 40 for B mode (two dimensional) echo and Doppler processing, respectively, are outlined in the flowcharts of FIGS. 6 and 7, respectively. The number in each flowchart block of FIGS. 6 and 7 refers to the numbered processor in the ASIC block diagram of FIG. 5.

The image frame memory 430 of the digital signal processing ASIC 40 shares a common architecture and implementation technology with the frame buffer memory of the back end ASIC 50. To take advantage of this commonality and the resultant efficiency in ASIC fabrication and density, the image frame memory 430 and its associated flash suppression processor 434 and IIR filter 436 can be located on the back end ASIC 50, thereby partitioning the digital signal processing ASIC and the back end ASIC at the output of FIR filter 432. Thus, the digital signal processing function of FIG. 5 up through the output of FIR filter 432, or all of the functions shown in FIG. 5 can be fabricated on a single integrated circuit chip, depending upon this partitioning choice and other integrated circuit layout considerations.

The back end ASIC 50 is the location of the RISC processor 502, which is used to coordinate the timing of all of the operations of the handheld ultrasound system. The RISC processor is connected to all other major functional areas of the ASICs to coordinate process timing and to load buffers and registers with the data necessary to perform the type of processing and display desired by the user. Program data for operation of the RISC processor is stored in a program memory 52 which is accessed by the RISC processor. Timing for the RISC processor is provided by clock signals from the clock generator located on the front end ASIC 30. The RISC processor also communicates through a PCMCIA and/or infrared transmitter interface, by which the processor can access additional program data or transmit image information remotely. The interface can connect to a telemetry link or a modem for the transmission of ultrasound images from the handheld unit to a remote location, for instance.

The RISC processor is operated under user control by commands and entries made by the user on the user control 70. A chart showing control functions, the type of controls, and their description is shown in FIG. 8. It will be appreciated that a number of functions, such as patient data entry, Cineloop operation, and 3D review, will operate through menu control to minimize the number of key or button controls on the small handheld unit. To further simplify the unit a number of operating functions are preprogrammed to specific diagnostic applications and will operate automatically when a specific application is selected. Selection of B mode imaging will automatically invoke frequency compounding and depth dependent filtering on the digital signal processing ASIC 40, for instance, while a four multiplier filter will automatically be set up as a wall filter on the DSP ASIC when Doppler operation is selected. The menu selection of specific clinical applications can automatically invoke specific feature settings such as TGC control characteristics and focal zones, for example.

What is claimed is:

1. In a handheld ultrasound device including a transducer, beamformer, and image processor, a digital signal processor comprising:

a digital B mode filter for filtering B mode signals;

a digital Doppler filter for filtering Doppler signals;

a B mode signal detection and mapping circuit;

a Doppler signal estimator circuit, and a PCMCIA interface for receiving a removable memory.

2. In the handheld ultrasound device of claim 1, wherein said digital filters, said B mode signal detection and mapping circuit, and said Doppler signal estimator circuit are located on a digital signal processing integrated circuit chip.

3. In the handheld ultrasound device of claim 1, wherein common elements of said digital signal processor are used for Doppler processing of Doppler signals, and also for B mode processing of B mode signals.

4. In the handheld ultrasound device of claim 3, wherein said common elements include elements of said digital filters.

5. In the handheld ultrasound device of claim 4, wherein said digital signal processor is adopted to configure said digital filters such that they can be operated both as a bandpass filter for B mode signals, and as a high pass filter for Doppler signals.

6. In the handheld ultrasound device of claim 4, wherein said digital signal processor is adopted to configure said digital filters such that they can be operated both as a bandpass filter for B mode signals and as a wall filter for Doppler signals.

7. In the handheld ultrasound device of claim 1, wherein said digital signal processor further includes a normalization circuit for normalizing variations in the transducer aperture.

8. In the handheld ultrasound device of claim 1, wherein said digital signal processor further includes means for forming a synthetic aperture.

9. In the handheld ultrasound device of claim 1, wherein said digital signal processor further includes a depth dependent filter.

10. In the handheld ultrasound device of claim 1, wherein said digital signal processor further includes a speckle reduction circuit.

11. In the handheld ultrasound device of claim 1, wherein said digital signal processor further includes a flash suppression circuit for Doppler signals.

12. In the handheld ultrasound device of claim 1, wherein said digital signal processor further includes means for assembling scanlines from multiple focal zones.

\* \* \* \* \*